United States Patent [19]

Lilje

[11] Patent Number: 4,667,031

[45] Date of Patent: May 19, 1987

[54] PROCESS FOR PREPARING OXAZEPINONES

[75] Inventor: Kenneth C. Lilje, Baton Rouge, La.

[73] Assignee: Ethyl Corporation, Richmond, Va.

[21] Appl. No.: 787,462

[22] Filed: Oct. 15, 1985

[51] Int. Cl.[4] .................. C07D 267/14; C07D 267/08; C07D 281/10; C07D 281/04
[52] U.S. Cl. ..................................... 540/490; 540/488
[58] Field of Search ................. 260/239.3 B, 239.3 T; 540/488, 490

[56] References Cited

FOREIGN PATENT DOCUMENTS 0107930  5/1984  European Pat. Off. ...... 260/239.8 B

OTHER PUBLICATIONS

March "Advanced Organic Chemistry" 2nd edition, (McGraw Hill), p. 633.

Primary Examiner—Robert T. Bond
Attorney, Agent, or Firm—Donald L. Johnson; John F. Sieberth; Patricia J. Hogan

[57] ABSTRACT

Oxazepinones and thiazepinones corresponding to the formula:

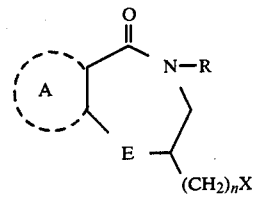

are prepared by mixing an alkali metal salt corresponding to the formula

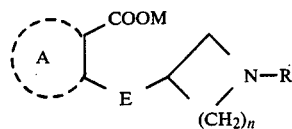

with oxalyl chloride or bromide in an inert solvent and heating to effect halogenation and fusion, A in the formulas representing a substituted or unsubstituted benzene, naphthalene, or pyridine ring bearing up to two Y substituents; E being oxygen or sulfur; R being an alkyl, cycloalkyl, or phenalkyl group or a substituted phenalkyl group bearing up to two ar-Y substituents; X being chloro or bromo; M being an alkali metal; n being one or two; and Y being a substituent selected from alkyl, alkoxy, trifluorimethyl, nitro, and halo. The products are useful as pharmaceutical intermediates.

19 Claims, No Drawings

PROCESS FOR PREPARING OXAZEPINONES

FIELD OF THE INVENTION

This invention relates to aromatic 2,3-dihydro-1,4-oxazepin-5(4H)-ones, sulfur analogs thereof, and more particularly a process for preparing them.

GLOSSARY

For convenience the terms defined below or obvious variations thereof are sometimes used in the specification to designate the indicated compounds. Any letter used in the general formulas to designate an element or group has the same meaning in each of the formulas in which it is used.

1. AROMATIC 2,3-DIHYDRO-1,4-OXAZEPIN-5(4H)-ONES AND SULFUR ANALOGS THEREOF—(a) compounds corresponding to the formula:

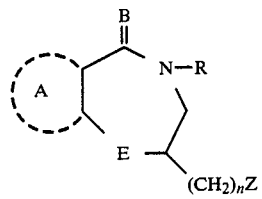

wherein the flat-sided circle A, hereinafter designated as A, represents a substituted or unsubstituted benzene, naphthalene, or pyridine ring bearing up to two Y substituents; B and E are independently selected from oxygen and sulfur; R is an alkyl, cyclalkyl, or phenalkyl group or a substituted phenalkyl group bearing up to two ar-Y substituents; n is one or two; and Z is X or T; Y being a substituent selected from alkyl, alkoxy, trifluoromethyl, nitro, and halo (i.e., chloro, bromo, fluoro, or iodo); X being chloro or bromo; and T being an amino group selected from 1H-pyrazol-1-yl, 1H-imidazol-1-yl, and -NR'R" in which R' and R" may be separate groups independently selected from hydrogen and the groups that can be represented by R or may, together with the nitrogen, form a heterocyclic group selected from 1-pyrrolidin-1-yl, 2,5-dimethylpyrrolidin-1-yl, 2-methylpyrrolidin-1-yl, 1-piperidinyl, 4-substituted piperidin-1-yl, 4-morpholinyl, 1-piperazinyl, 4-substituted piperazin-1-yl, and 1,2,3,6-tetrahydropyridin-1-yl. (b) pharmaceutically-acceptable salts of the above compounds wherein Z is T.

2. AROMATIC 2-AMINOALKYL-2,3-DIHYDRO-1,4-OXAZEPIN-5(4H)-ONES AND SULFUR ANALOGS THEREOF—(a) compounds corresponding to the above formula wherein Z is T. (b) pharmaceutically-acceptable salts of such compounds.

3. AROMATIC 2-HALOALKYL-2,3-DIHYDRO-1,4-OXAZEPIN-5(4H)-ONES AND SULFUR ANALOGS THEREOF—compounds corresponding to the above formula wherein Z is X.

4. ALKALI METAL SALTS—compounds corresponding to the formula:

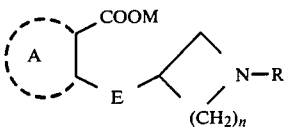

wherein M is an alkali metal.

5. PRECURSOR ACIDS—compounds corresponding to the formula:

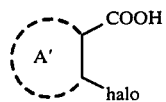

wherein A' is a substituted or unsubstituted pyridine ring bearing up to two Y substituents.

6. PRECURSOR ALCOHOLS—compounds corresponding to the formula:

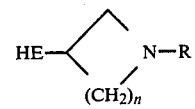

As used in this specification, the terms "alkyl" and "alkoxy" designate such groups containing 1–8 carbons, such as methyl, ethyl, propyl, isopropyl, butyl, sec-butyl, t-butyl, amyl, isoamyl, hexyl, heptyl, octyl, etc., and the corresponding alkoxy groups. The term "cycloalkyl" designates a cycloalkyl group containing 3–9 carbons, such as cyclopropyl, cyclobutyl, cyclopentyl, cyclohexyl, methylcyclohexyl, cycloheptyl, etc. The term "pharmaceutically-acceptable salt" is used in its usual sense to designate an acid addition salt, hydrate, alcoholate, or quaternary salt which is physiologically compatible in warm-blooded animals, including the salts of strong acids, such as hydrochloric, sulfuric, and phosphoric acids, and the salts of weak acids, such as fumaric, maleic, succinic, oxalic, citric, tartaric, and cyclohexamic acids, etc.

BACKGROUND

As disclosed in European Patent Application No. 0107930 (Cale et al.), it is known that aromatic 2-aminoalkyl-2,3-dihydro-1,4-oxazepin-5(4H)-ones and sulfur analogs thereof are compounds which are useful as antihistamines and which can be prepared, e.g., by (1) reacting a precursor acid with a precursor alcohol in the presence of a sodium compound, (2) halogenating and fusing the resultant alkali metal salt, (3) optionally thiating the aromatic 2-haloalkyl-2,3-dihydro-1,4-oxazepin-5(4H)-one or 1,4-thiazepin-5(4H)-one thus prepared, (4) aminating the ketone product of step 2 or the thione product of step 3, and (5) when desired, quaternizing the resultant amine or reacting it with a suitable acid to form a pharmaceutically-acceptable salt. This process, like the other processes taught by Cale et al. for the preparation of their pharmaceuticals, is effective but has the disadvantages of requiring multiple isolations of intermediates and typically providing the product in low yield.

An important factor leading to this low yield appears to be the inefficiency of the halogenation/fusion operation. The relevant working examples of Cale et al., i.e., Intermediates 1–9, show that their various halogenation/fusion reactions result in yields of only 23–60%, based on the starting materials for those reactions, and only about 1–27%, based on the amount of precursor acid or equivalent employed in the previous step. The patentees teach that other halogenating agents, such as phosphorus pentahalides, phosphorus trihalides, and triphenylphosphine dihalides, can be used in their reaction, but their teachings also indicate that other halogenating agents would be inferior to their preferred thionyl halides and combinations of triphenylphosphine with a carbon tetrahalide.

March, *Advanced Organic Chemistry*, Second Edition, McGraw-Hill, New York, page 633, teaches that oxalyl chloride has been used as a halogenating agent.

SUMMARY OF THE INVENTION

An object of this invention is to provide a novel process for halogenating and fusing an alkali metal salt to form an aromatic 2-haloalkyl-2,3-dihydro-1,4-ox- or thiazepin-5(4H)-one.

Another object is to provide such a process capable of producing the product in high yields.

A further object is to implement the process in an improved multi-step process for preparing aromatic 2-aminoalkyl-2,3-dihydro-1,4-oxazepin-5(4H)-ones and sulfur analogs thereof.

These and other objects are attained by mixing an alkali metal salt, as previously defined, with an oxalyl halide selected from oxalyl chloride and oxalyl bromide in an inert solvent and heating to effect halogenation and fusion so as to form an aromatic 2-haloalkyl-2,3-dihydro-1,4-ox- or thiazepin-5(4H)-one and, if desired, converting the product to an aromatic 2-aminoalkyl-2,3-dihydro-1,4-oxazepin-5(4H)-one or a sulfur analog thereof.

DETAILED DESCRIPTION

As indicated above, the alkali metal salt employed in the practice of the invention may be any alkali metal salt corresponding to the formula:

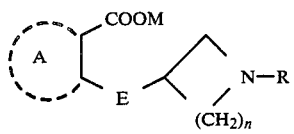

wherein A, E, R, n, and M have the same meanings as given above. The alkali metal salt may be a salt of any alkali metal but is generally a salt of sodium, potassium, or lithium, preferably sodium. In other preferred embodiments, A is a pyridine ring, most preferably a 3-pyridine; E is oxygen; R is methyl, ethyl, hexyl, or benzyl; and n is 2.

Exemplary of suitable salts are the sodium, potassium, and lithium salts of 4-chloro-2-[(1-methyl-3-pyrrolidinyl)oxy]benzoic acid, 5-bromo-2-[(1-methyl-3-pyrrolidinyl)oxy]benzoic acid, 5-methoxy-2-[(1-methyl-3-pyrrolidinyl)oxy]benzoic acid, 3,5-diiodo-2-[(1-methyl-3-pyrrolidinyl)oxy]benzoic acid, 2-[(1-substituted-3-pyrrolidinyl)oxy]benzoic acids wherein the 1-substituent is methyl, ethyl, isopropyl, cyclohexyl, benzyl, 4-chlorobenzyl, 4-methylbenzyl, 3,5-dimethoxybenzyl, 3-trifluoromethylbenzyl, 4-nitrobenzyl, etc., 3-[(1-methyl-3-pyrrolidinyl)oxy]-2-naphthoic acid, 2-[(1-substituted-3-pyrrolidinyl)oxy]-3-pyridine carboxylic acids wherein the 1-substituent is methyl, ethyl, isopropyl, cyclohexyl, benzyl, 4-chlorobenzyl, 4-methylbenzyl, 4-methoxybenzyl, 3-trifluoromethylbenzyl, 4-nitrobenzyl, etc., 3-[(1-methyl-3-pyrrolidinyl)oxy]-4-pyridine carboxylic acid, 4-[(1-methyl-3-pyrrolindinyl)oxy]-3-pyridine carboxylic acid, 3-[(1-methyl-3-pyrrolidinyl)oxy]-2-pyridine carboxylic acid, 2-[(1-methyl-3-pyrrolidinyl)thio]-3-pyridine carboxylic acid, 2-[(1-methyl-3-azetidinyl)oxy]-3-pyridine carboxylic acid, 2-[(1-cyclohexyl-3-azetidinyl)oxy]-3-pyridine carboxylic acid, etc. A particularly preferred salt is sodium 2-[(1-methyl-3-pyrrolidinyl)oxy]-3-pyridine carboxylate.

SYNTHESIS OF ALKALI METAL SALT

When not available, the alkali metal salts can be prepared by conventional means, such as the syntheses of Cale et al., the teachings of which are incorporated herein in toto by reference. The syntheses are preferably conducted in the same solvent as will later be used in the halogenation/fusion reaction. When the alkali metal salts are pyridine compounds, a preferred method of synthesizing the compounds comprises reacting a precursor acid corresponding to the formula:

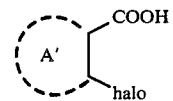

with a precursor alcohol corresponding to the formula:

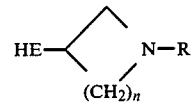

in an inert solvent and in the presence of a non-nucleophilic alkali metal base, such as sodium or other alkali metal diisopropyl amide, sodium or other alkali metal hydride, etc. The acid and alcohol are usually reacted in substantially stoichiometric amounts, although either reactant can be employed in excess; and the hydride or other alkali metal base is preferably employed in an amount sufficient to react with all of the hydroxyl groups of the acid and alcohol. The temperature employed for the reaction does not appear to be critical but is most commonly in the range of about 50°–150° C. and is preferably the reflux temperature of the solvent employed.

The particular acids and alcohols employed in the reaction vary, of course, with the particular acid and alcohol moieties desired in the alkali metal salts, generally and most conveniently being the acids and alcohols that are the direct sources of those moieties. As indicated by the formula, the required substituent that is ortho to the carboxyl group of the acid may be any halo substituent, but availability and cost factors make the o-chloro and o-bromo acids the generally preferred acids, with the o-chloro compounds being most preferred.

Exemplary of the precursor acids that may be used are 2-chloronicotinic acid, 3-chloro-4-pyridine carboxylic acid, 4-chloro-3-pyridine carboxylic acid, 3-chloro-2-pyridine carboxylic acid, etc. Suitable precursor alcohols include, e.g., the 1-substituted-3-pyrrolidinols, 1-substituted 3-azetidinols, and corresponding thiols wherein the 1-substituent is methyl, ethyl, isopropyl, cyclohexyl, benzyl, 4-chlorobenzyl, 4-methylbenzyl, 3,5-dimethoxybenzyl, 3-trifluoromethylbenzyl, 4-nitrobenzyl, etc.

The solvent employed in the salt-forming reaction may be any inert solvent. However, in a preferred embodiment of the invention, the solvent used in the preparation of the alkali metal salt is one that will also be suitable for use in the halogenation/fusion reaction of the invention and in subsequent reactions that will be conducted when an aromatic 2-aminoalkyl-2,3-dihydro-1,4-oxazepin-5(4H)-one or sulfur analog thereof is desired. Such solvents include, e.g., aromatic hydrocarbons such as benzene, toluene, xylene, etc.; ethers such as diethyl ether, tetrahydrofuran, dioxane, etc. Aromatic hydrocarbons such as toluene are generally preferred, and it is also preferred that the solvent have a boiling point in the range of about 50°–150° C.

HALOGENATION/FUSION REACTION

The halogenation/fusion reaction of the invention can be generally described as being the same as the halogenation/fusion reaction of Cale et al. except for the use of oxalyl chloride or oxalyl bromide as the halogenating agent. Thus, it is accomplished by mixing the alkali metal salt with the oxalyl halide in an inert solvent and heating at a suitable temperature to effect halogenation and, when necessary, subsequently neutralizing or basifying the halogenated compound, preferably with a tertiary amine such as triethylamine, and heating to effect fusion. In the preferred processes of the invention which utilize alkali metal salts wherein A is a pyridine ring, there is no need to use a tertiary amine or other fusion-inducing agent to effect fusion: the tendency toward fusion is so great that fusion inherently results from the conditions of the halogenation reaction. However, when the alkali metal salt is a compound in which A is a benzene or naphthalene ring, the added fusion-inducing agent is apt to be necessary.

The amount of oxalyl halide employed in the reaction does not appear to be critical, but best results are apt to be obtained when the halogenating agent is used in at least a stoichiometric amount. The preferred halogenating agent varies, of course, with the product desired. However, oxalyl chloride is ordinarily preferred.

The solvent employed in the halogenation/fusion reaction may be any inert solvent but is preferably a solvent, such as those mentioned above, which is also useful in the preparation of the alkali metal salt and in the preparation of derivatives of the 2-haloalkyl product of the halogenation/fusion reaction. As in the alkali metal salt syntheses, aromatic hydrocarbons such as toluene are generally preferred. Moreover, in a preferred embodiment of the invention, the solvent is the solvent in which the alkali metal salt was prepared and is incorporated by using, as the alkali metal salt, an alkali metal salt which is already suspended in the solvent in which it was prepared.

The temperature employed for the reaction does not appear to be critical but is most conveniently the reflux temperature of the solvent, e.g., a temperature in the range of about 50°–150° C.

When the halogenation/fusion reaction has been completed, the 2-haloalkyl product can be recovered by conventional means, such as the isolation techniques taught by Cale et al., if desired. However, in some cases, e.g., when the reaction is conducted as a step in a process for preparing another aromatic 2,3-dihydro-1,4-oxazepin-5(4H)-one or sulfur analog, it is preferred not to isolate the product but merely to remove the inorganic solids by filtration or a water wash and then to employ the solution of 2-haloalkyl compound in the subsequent reaction.

PREPARATION OF DERIVATIVES

The product of the halogenation/fusion reaction can be used in the preparation of other aromatic 2,3-dihydro-1,4-oxazepin-5(4H)-ones or sulfur analogs thereof by the procedures of Cale et al. or other suitable procedures. For example:

(1) the aromatic 2-haloalkyl-2,3-dihydro-1,4-ox- or thiazepin-5(4H)-one may be aminated with an amine corresponding to the formula TH to form the corresponding 2-aminoalkyl compound and then, if desired, converted to a pharmaceutically-acceptable salt, (2) the 2-haloalkyl compound or the corresponding 2-aminoalkyl compound may be thiated to the corresponding thione, and, in the case of the amino compound, converted to a pharmaceutically-acceptable salt, if desired, and (3) the 2-haloalkyl compound may be reacted with an alkali metal cyanide to form the corresponding 2-cyanoalkyl compound and then, if desired, reduced to a primary amine and converted to a pharmaceutically-acceptable salt.

In a preferred embodiment of the invention, the aromatic 2-haloalkyl-2,3-dihydro-1,4-ox- or thiazepin-5(4H)-one, still in the toluene or other solvent in which it was prepared, is thiated to the corresponding thione and then aminated with a TH amine to form the corresponding aromatic 2-aminoalkyl-2,3-dihydro-1,4-oxor thiazepine-5(4H)-thione, which, when desired, is then converted to a pharmaceutically-acceptable salt. This process is particularly advantageous when the thiation is accomplished by the process of copending application Ser. No. 770,603, filed Aug. 29, 1985, in the name of Kenneth C. Lilje, i.e., by reacting the 2-haloalkyl compound with phosphorus pentasulfide in the presence of an alkali metal bicarbonate and a hydrocarbon diluent. Such a process, with its improved halogenation/fusion and thiation steps, as well as its use of the same solvent until the 2-aminoalkyl compound has been formed, can result in product yields as high as about 60–65%, based on the amount of precursor acid initially employed. Thus, this overall process has a considerable advantage over the processes taught by Cale et al., whose yields have already been reduced to 27% or less by the time they have completed their halogenation/fusion step—a point in the reaction at which the present invention permits the attainment of yields as high as about 80%.

The following examples are given to illustrate the invention and are not intended as a limitation thereof.

EXAMPLE I

A 500 mL round-bottom flask equipped with a mechanical stirrer and reflux condenser was charged with 4.7 g of 60% NaH (2.5 g, 104 mmols NaH) and 150 mL of reagent grade toluene. To the stirred suspension was added 2-chloronicotinic acid (8.2 g, 52.1 mmols). Then a solution of 5.26 g (52.1 mmols) of 1-methyl-3-pyrrolidinol in 20 mL of toluene was added dropwise to the mixture. The suspension was for 90 minutes, after which oxalyl chloride (6.6 g, 52.1 mmols) in 20 mL of toluene was added. The resulting mixture refluxed for an additional 60 minutes, then cooled to ambient temperature. To the cooled suspension were added 25 mL of water 25 mL of 20% Na₂CO₃ solution. After 30 minutes the phases separated. The organic phase contained 10.0 g of 2-(2-chloroethyl)-2,3-dihydro-4-methylpyrido[3,2-f]-1,4-oxazepin-5(4H)-one, an 80% yield based on precursor acid. This solution can be concentrated to about 25-40% and used directly in the next step.

EXAMPLE II

To 70 mL of toluene under nitrogen were added 4.1 g (9.25 mmols) of phosphorus pentasulfide and 7.76 g (92.46 mmols) of sodium bicarbonate. The resulting suspension was warmed to 90° C. and stirred for 30 minutes. To the resulting suspension was added a toluene solution (41.3 g) containing 11.5 g (47.8 mmols) of 2-(2-chloroethyl)-2,3-dihydro-4-methylpyrido[3,2-f]-1,4-oxazepin-5(4H)-one dropwise over 40 minutes. The resulting mixture was heated to reflux. After one hour, tlc showed the starting material gone. The heat was removed and tetrahydrofuran (25 mL) was added to the warm suspension. After the mixture had cooled to ambient temperature, water (11 mL) was added, and stirring was continued for three hours. The resulting suspension was filtered. The organic phase in the filtrate was separated and found to contain 11.0 g of the desired oxazepinethione (90% yield). This solution is typically concentrated to 30-40% and used as is in the next example.

EXAMPLE III

A Fischer-Porter tube was charged with a mixture of 5 g (19.5 mmols) of 2-(2-chloroethyl)-2,3-dihydro-4-methylpyrido[3,2-f]-1,4-oxazepine-5(4H)-thione, 8.7 g of toluene, and 15 mL of dimethylamine. The mixture was allowed to stir overnight at ambient temperature. The reactor was opened and the contents transferred to a separatory funnel with 20 mL of additional toluene. The mixture was washed with a solution made from 3.1 g of 25% NaOH and 3.3 g of water. The organic phase was evaporated to a viscous yellow oil which was dissolved in 40 mL of acetone and filtered. To the clear solution was added 1.9 g of concentrated HCl. The resulting suspension was stirred overnight. The product was collected via filtration, washed with acetone, and air dried, giving 5.4 g (87% yield).

It is obvious that many variations can be made in the products and processes set forth above without departing from the spirit and scope of this invention.

What is claimed is:

1. In a process for preparing an oxazepinone or thiazepinone corresponding to the formula:

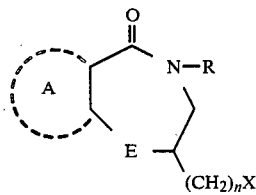

which comprises mixing an alkali metal salt corresponding to the formula:

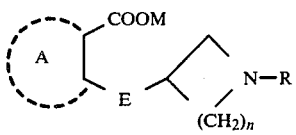

with a halogenating agent in an inert solvent and heating to effect halogenation and fusion, A in the formulas representing a substituted or unsubstituted benzene, naphthalene, or pyridine ring bearing up to two Y substituents; E being oxygen or sulfur; R being an alkyl, cycloalkyl, or phenalkyl group or a substituted phenalkyl group bearing up to two ar-Y substituents; X being chloro or bromo; M being an alkali metal; n being one or two; and Y being a substituent selected from alkyl, alkoxy, trifluoromethyl, nitro, and halo, the improvement which comprises employing an oxalyl halide selected from oxalyl chloride and oxalyl bromide as the halogenating agent.

2. The process of claim 1 wherein fusion is effected without the use of an added fusion-inducing agent.

3. The process of claim 1 wherein fusion is effected in the presence of a tertiary amine as a fusion-inducing agent.

4. The process of claim 1 wherein A is a pyridine ring.

5. The process of claim 4 wherein the alkali metal salt is a sodium, potassium, or lithium salt of an acid selected from 2-[(1-substituted-3-pyrrolidinyl)oxy]-3-pyridine carboxylic acids wherein the 1-substituent is methyl, ethyl, isopropyl, cyclohexyl, benzyl, 4-chlorobenzyl, 4-methylbenzyl, 4-methoxybenzyl, 3-trifluoromethylbenzyl, or 4-nitrobenzyl, 3-[(1-methyl-3-pyrrolidinyl)oxy]-4-pyridine carboxylic acid, 4-[(1-methyl-3-pyrrolidinyl)oxy]-3-pyridine carboxylic acid, 3-[(1-methyl-3-pyrrolidinyl)oxy]-2-pyridine carboxylic acid, 2-[(1-methyl-3-pyrrolidinyl)thio]-3-pyridine carboxylic acid, 2-[(1-methyl-3-azetidinyl)oxy]-3-pyridine carboxylic acid, and 2-[(1-cyclohexyl-3-azetidinyl)oxy]-3-pyridine carboxylic acid.

6. The process of claim 5 wherein the alkali metal salt is sodium 2-[(1-methyl-3-pyrrolidinyl)oxy]-3-pyridine carboxylate.

7. The process of claim 1 wherein the oxalyl halide is oxalyl chloride.

8. The process of claim 1 wherein the inert solvent is a solvent having a boiling point in the range of about 50°-150° C.

9. The process of claim 8 wherein the inert solvent is an aromatic hydrocarbon.

10. The process of claim 9 wherein the inert solvent is toluene.

11. The process of claim 1 wherein the reaction is conducted at a temperature of about 50°-150° C.

12. The process of claim 1 wherein a sodium, potassium, or lithium salt of a 2-[(1-substituted-3-pyrrolidinyl)oxy]-3-pyridine carboxylic acid wherein the 1-substituent is methyl, ethyl, isopropyl, cyclohexyl, benzyl, 4-chlorobenzyl, 4-methylbenzyl, 4-methoxybenzyl, 3-trifluoromethylbenzyl, or 4-nitrobenzyl, 3-[(1-methyl-3-pyrrolidinyl)oxy]-4-pyridine carboxylic acid, 4-[(1-methyl-3-pyrrolidinyl)oxy]-3-pyridine carboxylic acid, 3-[(1-methyl-3-pyrrolidinyl)oxy]-2-pyridine carboxylic acid, 2-[(1-methyl-3-pyrrolidinyl)thio]-3-pyridine carboxylic acid, 2-[(1-methyl-3-azetidinyl)oxy]3-pyridine carboxylic acid, or 2-[(1-cyclohexyl-3-azetidinyl)oxy]-3-pyridine carboxylic acid, is mixed with oxalyl chloride in an aromatic hydrocarbon solvent having a boiling point of about 50°–150° C. and heated at the reflux temperature to effect halogenation and fusion.

13. The process of claim 12 wherein the alkali metal salt is sodium 2-[(1-methyl-3-pyrrolidinyl)oxy]-3-pyridine carboxylate.

14. In a process for preparing an oxazepinone or thiazepinone corresponding to the formula:

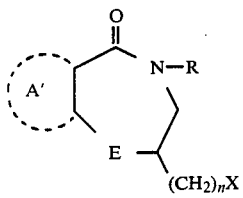

which comprises reacting a precursor acid corresponding to the formula:

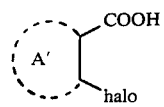

with a precursor alcohol corresponding to the formula:

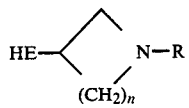

in an inert solvent and in the presence of a non-nucleophilic alkali metal base to form an alkali metal salt corresponding to the formula:

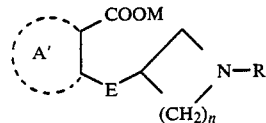

mixing the alkali metal salt with a halogenating agent in an inert solvent, and heating to effect halogenation and fusion, A' in the formulas representing a substituted or unsubstituted pyridine ring bearing up to two Y substituents; E being oxygen or sulfur; R being an alkyl, cycloalkyl, or phenalkyl group or a substituted phenalkyl group bearing up to two ar-Y substituents; X being chloro or bromo; M being an alkali metal; n being one or two; and Y being a substituent selected from alkyl, alkoxy, trifluoromethyl, nitro, and halo, the improvement which comprises preparing the halogenation/fusion reaction mixture by adding an oxalyl halide selected from oxalyl chloride and oxalyl bromide to the total reaction mixture resulting from the acid/alcohol reaction.

15. The process of claim 14 wherein the precursor acid is 2-chloronicotinic acid, the precursor alcohol is a 3-pyrrolidinol, and the inert solvent is an aromatic hydrocarbon having a boiling point of about 50°–150° C.

16. The process of claim 15 wherein the reactions are conducted at reflux temperature.

17. In a process for preparing a compound corresponding to the formula:

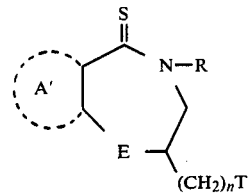

which comprises reacting a precursor acid corresponding to the formula:

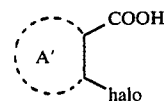

with a precursor alcohol corresponding to the formula:

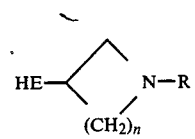

in an inert solvent and in the presence of a non-nucleophilic alkali metal base to form an alkali metal salt corresponding to the formula:

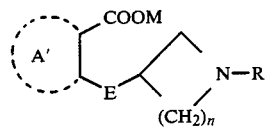

mixing the alkali metal salt with a halogenating agent in an inert solvent, heating to effect halogenation and fusion, thiating the resultant compound in an inert solvent to form a thione corresponding to the formula:

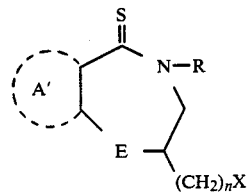

and reacting the thione with an amine corresponding to the formula TH, A' in the formulas representing a substituted or unsubstituted pyridine ring bearing up to two Y substituents; E being oxygen or sulfur; R being an alkyl, cycloalkyl, or phenalkyl group or a substituted phenalkyl group bearing up to two ar-Y substituents; T being an amino group selected from 1H-pyrazol-1-yl, 1H-imidazol-1-yl, and -NR'R" in which R' and R" may be separate groups independently selected from hydrogen and the groups that can be represented by R or may, together with the nitrogen, form a heterocyclic group selected from 1-pyrrolidin-1-yl, 2,5-dimethylpyrrolidin-1-yl, 2-methylpyrrolidin-1-yl, 1-piperidinyl, 4-substituted piperidin-1-yl, 4-morpholinyl, 1-piperazinyl, 4-substituted piperazin-1-yl, and 1,2,3,6-tetrahydropyridin-1-yl; X being chloro or bromo; M being an alkali metal; n being one or two; and Y being a substituent selected from alkyl, alkoxy, trifluoromethyl, nitro, and halo, the improvement which comprises employing an oxalyl halide selected from oxalyl chloride and oxalyl bromide as the halogenating agent and conducting the series of reactions without isolating the intermediates from the reaction mixtures.

18. The process of claim 17 wherein the precursor acid is 2-chloronicotinic acid, the precursor alcohol is a 3-pyrrolidinol, and the inert solvent is an aromatic hydrocarbon having a boiling point of about 50°–150° C.

19. The process of claim 18 wherein the reactions are conducted at reflux temperature.

* * * * *